United States Patent [19]

Krespan et al.

[11] Patent Number: 5,929,293
[45] Date of Patent: Jul. 27, 1999

[54] PROCESS FOR THE PREPARATION OF FLUOROOLEFINS

[75] Inventors: Carl George Krespan, Wilmington; Viacheslav Alexandrovich Petrov, Hockessin, both of Del.

[73] Assignee: E. I. du Pont de Nemours and Company, Wilmington, Del.

[21] Appl. No.: 08/981,391

[22] PCT Filed: Jun. 25, 1996

[86] PCT No.: PCT/US96/10865

§ 371 Date: Dec. 29, 1997

§ 102(e) Date: Dec. 29, 1997

[87] PCT Pub. No.: WO97/02226

PCT Pub. Date: Jan. 23, 1997

Related U.S. Application Data

[60] Provisional application No. 60/000,734, Jun. 30, 1995.

[51] Int. Cl.⁶ ..................................................... C07C 17/02

[52] U.S. Cl. ................................................................ 570/153
[58] Field of Search ............................................... 570/153

[56] References Cited

U.S. PATENT DOCUMENTS

| | | |
|---|---|---|
| 3,192,274 | 6/1965 | Baranauckas et al. . |
| 3,377,390 | 4/1968 | Rondestvedt, Jr. et al. . |
| 3,557,224 | 1/1971 | Jaeger . |
| 4,073,817 | 2/1978 | Jager ........................................ 570/153 |
| 4,587,366 | 5/1986 | Werner .................................... 570/153 |

FOREIGN PATENT DOCUMENTS

| | | |
|---|---|---|
| 1 443 444 | 7/1976 | United Kingdom . |
| WO 95/16656 | 6/1995 | WIPO . |

*Primary Examiner*—Alan Siegel

[57] ABSTRACT

The invention concerns processes for the preparation of fluoroolefins, including a process for the deiodofluorination of an iodine containing fluorocarbon comprising contacting said iodine containing fluorocarbon with a fluoroolefin in the presence of an aluminum chlorofluoride catalyst.

23 Claims, No Drawings

PROCESS FOR THE PREPARATION OF FLUOROOLEFINS

This application is a 371 of PCT/US96/10865 field Jun. 25, 1996 and a continuation of provisional application NO. 60/000,734 filed Jun. 30, 1995.

FIELD OF THE INVENTION

This invention concerns processes for the preparation of fluoroolefins.

TECHNICAL BACKGROUND

U.S. Pat. No. 3,377,390 discloses compounds of the formula $R_fIF_x$ where x is an integer of two or four. This patent discloses that a compound of the formula $R_fIF_x$ will initiate telomerization of perfluoroalkyl iodides with certain olefins.

U.S. Pat. No. 3,557,224 discloses a process for the manufacture of perfluoroalkyl iodide telomers from the corresponding monomers by telomerizing a perfluoroalkyl iodide with a perfluoroethylene or a perfluoropropylene containing at least one Cl atom in the presence of a catalyst.

U.K. Patent No. 1,443,444 discloses a process for preparing bromine containing telomers.

SUMMARY OF THE INVENTION

This invention provides a process for the preparation of perfluorinated olefins of the structure $R_fCF=CFCF_3$ by the reaction of perfluoroalkyliodides of the structure $R_fCF_2I$, wherein $R_f$ is $C_nF_{2n}F$, wherein n is 1 to 12, with perfluoroolefins in the presence of an aluminum chlorofluoride catalyst.

Included herein is a process for the preparation of perfluorobutene-2 by the dimerization of tetrafluoroethylene, in the presence of an aluminum chlorofluoride/perfluoroalkyl iodide catalyst system.

This invention also provides a process for the deiodofluorination of an iodine containing fluorocarbon comprising contacting said iodine containing fluorocarbon with a fluoroolefin capable of picking up the elements of iodine monofluoride in the presence of an aluminum chlorofluoride catalyst (ACF).

DETAILED DESCRIPTION OF THE INVENTION

The processes of the present invention are illustrated by the following equations.

Equation 1
$$R_fCF_2I + CF_2=CF_2 \longrightarrow R_fCFICF_2CF_3$$

Equation 2

wherein $R_f$ in Equations 1 and 2 is $C_nF_{2n}F$ where n is 1–12, $R_{f'}$ is selected from F and $C_nF_{2n}F$ and $R_{f''}$ is selected from F and $CF_3$.

The iodine-containing starting compound is believed to add across the double bond of tetrafluoroethylene (TFE). The secondary perfluoroalkyl iodide formed in Equation 1 reacts, as shown in Equation 2, with a second molecule of TFE or with hexafluoropropene to generate the product olefin and a molecule of short-chain perfluoroalkyl iodide, $R_{f''}CFICF_3$ ($R_{f''}=CF_3$ or F). Perfluoroalkyl iodide generated in this reaction of perfluoroalkyl iodide with TFE (Eq 2, $R_{f'}=F$) competes with starting iodide $R_fCF_2I$ in the reaction with TFE.

The special case of equation 1 and 2 is the case where $R_fCF_2I$ is perfluoroethyl iodide. This reaction generates perfluoroethyl iodide (see Eq 3) and the process becomes catalytic in perfluoroethyl iodide.

Equation 3
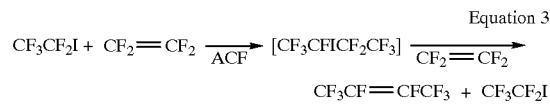

The process of Eq. 2, which involves the transfer of iodine monofluoride from a perfluoroalkyl iodide, can be carried out independently of Eq. 1 with primary or secondary perfluoroalkyl iodides using TFE or hexafluoropropylene (HFP) as perfluoroolefin (Eq. 2 and 4).

Equation 4
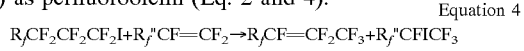

wherein $R_f$ in Equation 4 is $C_nF_{2n}F$ where n is 1–12 and $R_{f''}$ is F or $CF_3$.

The discussion below summarizes the embodiments exemplified in certain examples; however, the invention is not meant to be limited to these examples as equivalents are also intended to be included.

In Example 1, illustrating equations 1 and 2, $R_f$ is $CF_3$; and thus $R_fCF_2I$ is perfluoroethyl iodide. This is the special case cited above.

In Example 2, illustrating equations 1 and 2, $R_f$ is n-$C_3F_7$, $R_{f'}$ is F and thus $R_{f'}CF=CF_2$ is TFE. Because only 0.06 mole of perfluoro-n-butyl iodide is present versus 0.5 mole of TFE, and because perfluoroethyl iodide reacts faster than perfluoro-n-butyl iodide, the predominant products arise from the generated perfluoroethyl iodide competing successfully with perfluoro-n-butyl iodide. The major product is perfluorobutene-2.

In Example 3, as compared to Example 2, the molar ratio of perfluoro-n-butyl iodide to TFE is increased 2.1 times. Here, the products reflect less successful competition between perfluoroethyl iodide and perfluoro-n-butyl iodide. A major product is perfluoroethyl iodide and the amount of perfluorohexenes is increased.

In Example 4, perfluoro-n-butyl iodide ($R_f$=n-$C_3F_7$) and hexafluoropropene ($R_{f'}$ in $R_{f'}CF=CF_2$ is $CF_3$) yield perfluoro-butene-2 and perfluoroisopropyliodide. This is an example of Equation 4 of this invention.

In Example 5, perfluoro-n-hexyliodide ($R_f$=n-$C_5F_{11}$) with hexafluoropropene yields perfluorohexene-2 and perfluorohexene-3 (in the ratio of 23:77) and perfluoroisopropyl iodide. This is an example of Equation 4.

Example 6, demonstrates scaled-up synthesis and isolation of perfluorobutene-2.

The process of equation 2 can be operated together with equation 1 or independently of equation 1.

For the process of Equation 2 practiced independently of Equation 1 or the process of Equation 4, solvents or diluents may be employed in the present process. The solvent or diluent should not be reactive in the process or lead to the deactivation of the aluminum chlorofluoride catalyst. Said solvents or diluents can be perfluoroalkanes or perfluorocycloalkanes, for example, perfluorocyclobutane or the cyclic dimer of hexafluoropropene, i.e., the isomeric perfluorodimethylcyclobutanes; perfluoroethers or perfluoro tertiary amines. Preferred on the basis of ready availability is the cyclic dimer of hexafluoropropene.

The temperature employed in the process of the present invention ranges from about 20 degrees to about 200 degrees centigrade. The preferred temperature range is about 50° C. to 150° C.

Reaction time is not critical and ranges from about 2 to about 24 hours. Overnight reactions, i.e., about 16 hours, are convenient.

Pressure of the reaction is not critical. Autogenous pressures are usually employed.

Since the reaction conditions are heterogeneous, some degree of agitation is usually applied.

The reaction is carried out in the presence of an aluminum halide Lewis acid catalyst, wherein the aluminum halide is a mixed halide containing F and at least one of Cl, Br or I. Preferred catalysts are of the structure $AlF_nCl_{3-n}$, wherein n is from 0.05 to 2.95. Preferably n is from 2.5 to 2.95. Fluorinated aluminum chloride catalysts can be prepared by the reaction of $AlCl_3$ and $CFCl_3$ according to the method described in U.S. Pat. No. 5,162,594, column 4, line 35–57, which is hereby incorporated by reference. Catalysts may be preformed or may be generated in situ.

Since the catalyst is water sensitive, reagents and equipment should be dried before use.

The proportion of catalyst to $R_fCF_2I$ is 0.1 to 20 weight percent.

Product can be isolated by conventional means, for example, fractionation.

When the processes of Equations 1 and 2 are carried out sequentially, the temperature range of −10° C. to 200° C. is employed. Where $R_f''$ is F, a preferred temperature range is about −10° C. to 100° C.. Where $R_f''$ is $CF_3$, the preferred temperature range is 50° C. to 150° C.

Reaction time is not critical and ranges from about 2 to about 24 hours. Overnight reactions, i.e., about 16 hours, are convenient.

Solvents or diluents may be employed in the present process. The solvent or diluent should not be reactive in the process or lead to the deactivation of the aluminum chlorofluoride catalyst. Said solvents or diluents a can be perfluoroalkanes or perfluorocycloalkanes, for example, perfluorocyclobutane or the cyclic dimer of hexafluoropropene, i.e., the isomeric perfluorodimethylcyclobutanes; perfluoroethers or perfluoro tertiary amines. Preferred on the basis of ready availability is the cyclic dimer of hexafluoropropene.

Pressure of the reaction is not critical. Autogenous pressures are usually employed.

Since the reaction conditions are heterogeneous, some degree of agitation is usually applied.

The reaction is carried out in the presence of an aluminum halide Lewis acid catalyst, wherein the aluminum halide is a mixed halide containing F and at least one of Cl, Br or I. Preferred catalysts are of the structure $AlF_nCl_{3-n}$, wherein n is from 0.05 to 2.95. Preferably n is from 2.5 to 2.95. Fluorinated aluminum chloride catalysts can be prepared by the reaction of $AlCl_3$ and $CFCl_3$ according to the method described in U.S. Pat. No. 5,162,594, column 4, line 35–57, which is hereby incorporated by reference. Catalysts may be preformed or may be generated in situ.

Since the catalyst is water sensitive, reagents and equipment should be dried before use.

The proportion of $R_fCF_2I$ to $R_fCF=CF_2$ is between 1:1 and 1:1000 on a molar basis. The amount of $AlF_nCl_{3-n}$ to $R_fCF_2I$ is between 0.1 and 20% on a weight basis.

This process provides a practical route to the highly desirable fluoroolefin of the structure $CF_3CF=CFCF_3$ (perfluorobutene-2). Such olefins are used as intermediates for synthesis of the environmentally friendly HFC's.

Product can be isolated by conventional means, for example, fractionation. In the case of perfluorobutene-2, it is advantageous to use a solvent capable of coordinating or complexing one of the components, perfluoroethyl iodide or perfluorobutene-2, preferentially during isolation. Useful solvents are acetonitrile, dimethylformamide, dimethylacetamide, glymes, hexamethylphosphoramide, aromatic hydrocarbons, dinitriles such as adiponitrile, and ureas. Preferred solvents are acetonitrile, dimethylformamide, dimethylacetamide, glymes, adiponitrile, benzene and toluene.

This invention further provides an azeotrope of perfluorobutene-2 and perfluoroethyliodide in the ratio of 85:15 and a process for preparing said azeotrope. Also provided is a method for breaking said azeotrope by distillation from a mixture containing a solvent capable of forming a complex with perfluoroethyl iodide or perfluorobutene-2 as discussed above.

EXAMPLES

Catalyst Preparation—$AlCl_3+CFCl_3$ 500 g (3.75 mol) of $AlCl_3$ (Aldrich-99% pure) was stirred mechanically under $N_2$ in a r.b. flask fitted with a −80° C.. condenser while 1750 mL (~2625 g, 19 mol) of $CFCl_3$ was added over a 1.5-hr period. Reaction is very exothermic in the early stages, so addition of $CFCl_3$ was slow at first in order to keep the temperature below 65° C., then rapid. The resulting suspension was stirred an additional 3 hrs while volatiles ($CF_2Cl_2$) were allowed to escape through the warmed condenser. The condenser was then replaced with a simple stillhead, and most of the $CCl_4$ was distilled under reduced pressure [mainly bp 38° C. (200 mm)]. Finally, the last traces of volatiles were removed by warming the residual solid to 30–35° C. at 0.05 mm.

The sealed r.b. flask was transferred to a dry box and unloaded into a Teflon® FEP bottle; 340 g of rather finely divided yellow-green solid. Portions of the catalyst were weighed out in the dry box as needed and taken out in plastic bottles with pressure-seal caps.

Analysis for fluorine of the products from preparation of this type indicated the composition to be $AlF_{2.9}Cl_{0.1}$, $AlF_xCl_y$; X=2.8–2.9, Cl=0.2-0.1.

Example 1

Preparation of perfluorobutene-2 (from perfluoroethyl iodide and TFE)

A 240 mL Hastelloy shaker tube was flushed with nitrogen, then loaded with 5 g of aluminum chlorofluoride catalyst, cooled to −78C, evacuated and loaded with 40g (0.16 mole) of perfluoroethyl iodide and 40 g (0.4 mole) of tetrafluoroethylene. The reaction vessel was allowed to warm and kept on a shaker at 25–30° C. at autogenous pressure. Significant pressure drop (approximately 150 psi) was observed in the first 2 hours. After 18 hours, the pressure tube was unloaded. The product, 55 g, was collected in a −78° C. cold trap. According to $^{19}F$ NMR, it was a mixture of 41% of perfluoroethyl iodide (recovered starting material) and 59% of perfluorobutene-2, mixture of cis and trans isomers in a 3:2 ratio. The calculated yield of perfluorobutene-2 based on converted perfluoroethyl iodide was 82.5%.

Example 2

Preparation of perfluorobutene-2 (from perfluorobutyl iodide and TFE)

A 240 mL Hastelloy shaker tube was flushed with nitrogen, then loaded with 5 g of aluminum chlorofluoride catalyst, cooled to −78° C., evacuated and loaded with 20 g (0.06 mole) of perfluorobutyl iodide and 50 g (0.5 mole) of tetrafluoroethylene. The reaction vessel was allowed to warm and kept on a shaker at 25–30° C. at autogenous pressure. Significant pressure drop (approximately 150 psi) was observed in the first 2 hours. After 18 hours, the pressure tube was unloaded. The product, 40 g, was collected in a −78° C. cold trap. According to $^{19}$F NMR, it was a mixture of 90% of perfluorobutene-2, mixture of cis and trans isomers in a 3:2 ratio and 10% of perfluoroethyl iodide. The calculated yield of perfluorobutene-2 based on converted perfluorobutyl iodide was 72%. According to $^{19}$F NMR, the main component (about 70%) of the residue (15 g) was a mixture of perfluorohexene-2, (minor) and perfluorohexene-3.

Example 3

Reaction of perfluorobutyl iodide with TFE

A 240 mL Hastelloy shaker tube was flushed with nitrogen, then loaded with 5 g of aluminum chlorofluoride catalyst, cooled to −78° C., evacuated and loaded with 34 g (0.1 mole) of perfluorobutyl iodide and 40 g (0.4 mole) of tetrafluoroethylene. The reaction vessel was allowed to warm and kept on a shaker at 25–30° C. at autogenous pressure. Significant pressure drop (approximately 150 psi) was observed in the first 2 hours. After 18 hours, the pressure tube was unloaded. The crude product, 58 g, was collected in a −78° C. cold trap. According to $^{19}$F NMR, it was a mixture of 40% of perfluoroethyl iodide, 25% of perfluorobutene-2, 20% of perfluorohexene-3, 10% of perfluorobutyl iodide and 5% of perfluorohexene-2. The calculated yield of perfluorohexenes based on converted perfluorobutyl iodide was 51%. The calculated yield of perfluorobutene-2 based on converted perfluorobutyl iodide was 38%.

Example 4

Reaction of perfluorobutyl iodide with hexafluoropropene

A 240 mL Hastelloy shaker tube was flushed with nitrogen, then loaded with 3.5 g of aluminum chlorofluoride catalyst, cooled to −78° C., evacuated and loaded with 34.6 g (0.1 mole) of perfluorobutyl iodide and 15 g (0.1 mole) of hexafluoropropene. The reaction vessel was heated to 80° C. and kept on a shaker at 80° C. autogenous pressure for 24 hours. After 24 hours, the contents of the first shaker tube was transferred to a second shaker tube containing 3.5 g of aluminum chlorofluoride catalyst. Additional hexafluoropropene, 7.5 g 0.05 mole, was added and the tube was shaken at 80° C. for 48 hours. The crude product was according to gas chromatography and $^{19}$F NMR, a mixture of perfluorobutene-2 and perfluoroisopropyl iodide. Upon distillation, 10 g of material with boiling point −3 to +2° C. was obtained that was according to $^{19}$F NMR 97% pure perfluorobutene-2, mixture of cis and trans isomers in a 81:19 ratio. The residue (33 g) according to $^{19}$F NMR contained 71% of perfluoroisopropyl iodide, 13% of perfluorobutene-2 and 16% of perfluorobutyl iodide starting material and a small amount of 2-iodoperfluorobutane as a contaminant. The calculated yield of perfluorobutene-2 was 84%, the calculated yield of perfluoroisopropyl iodide was 80%.

Example 5

Reaction of perfluoro-n-hexyliodide with hexafluoropropene

Perfluoro-n-hexyl iodide, 4.5 g (0.01 mole) and 0.5 g of aluminum chlorofluoride catalyst were placed in a heavy walled Pyrex® glass sample tube equipped with a Teflon® stopcock. The sample tube was evacuated at −196° C. and 1.5 g (10 mmole) of hexafluoropropene was added through the vacuum line. The sample tube was placed in a shielded heater and heated to 75° C. for 10 hours. The tube was cooled to 0° C., opened and the reaction mixture was poured into water. The organic (lower) layer was separated and dried over phosphorous pentoxide. The product, 5.8 g was a mixture of 49% of perfluoroisopropyl iodide, 48% of a mixture of perfluorohexene-2 and perfluorohexene-3 (in the ratio of 23:77) contaminated with a small amount of (2–3%) of an unidentified product, probably 3-iodo perfluoro-n-nonane. The calculated yield of perfluorohexenes was 93%; the calculated yield of perfluoroisopropyl iodide was 95%.

Example 6

Preparation of perfluorobutene-2 by catalytic dimerization of TFE

The reaction was scaled up in a 1L Hastelloy stirred autoclave which was loaded with 20 g ACF and 100 g of $C_2F_5I$. TFE was added at 30–35° C. in 20 to 30 g increments. After addition of 400–600 g of TFE the clave was unloaded, a new portion (100 g) of $C_2F_5I$ was added and the cycle was repeated. Using 20 g of ACF and 200 g total of $C_2F_5I$, 980 g of TFE was consumed in this reaction.

The distillation of crude product gave 650 g of an azeotropic mixture comprising 85% of $CF_3CF=CFCF_3$ and 15% of $C_2F_5I$ (b.p. 0–1° C.), and 220 g of higher b.p. material.

The yield of $CF_3CF=CFCF_3$ was 57%. The separation of $CF_3CF=CFCF_3$ and $C_2F_5I$ was achieved by distillation of a mixture with dry dimethylacetamide. After the first distillation [350 g of mixture of $CF_3CF=CFCF_3/C_2F_5I$ (85:15); 200 mL $(CH_3)_2NC(O)CH_3$] 253 g of $CF_3CF=CFCF_3$ containing 2% of $C_2F_5I$ was obtained.

Second distillation [300 g of 98:2 mixture of $CF_3CF=CFCF_3$ and $C_2F_5I$, 100 mL of $(CH_3)_2NC(O)CH_3$] gave 210 g of perfluorobutene-2 (trans: cis=4:1), containing, according to GC, 0.2% of $C_2F_5I$.

The product with higher b.p. obtained in this reaction (220 g) was distilled giving 143 g of material with b.p. 50–52° C. and 24 g of residue. According to $^{19}$F NMR the main fraction was a mixture of the following compounds: $CF_3CF=C(CF_3)C_2F_5$ cis 38%, trans 9.5%; $CF_3CF=CFC_3F_7$ cis 2%, trans 7%, $C_2F_5CF=CFC_2F_5$ cis 5%, trans 29%; $CF_3CFICF_2CF_3$ 9.5%.

What is claimed is:

1. A process for the deiodofluorination of an iodine-containing fluorocarbon comprising:

contacting an iodine-containing fluorocarbon with a fluoroolefin that is of the structure $R_f''CF=CF_2$, wherein $R_f''$ is selected from the group consisting of F and $CF_3$, in the presence of an aluminum chlorofluoride catalyst.

2. The process of claim 1 wherein the iodine containing fluorocarbon is of the structure $R_fCFICFR_f'CF_3$ or $R_fCF_2CF_2CF_2I$ wherein $R_f$ is $C_nF_{2n}F$, wherein n is 1 to 12 and $R_f'$ is F or $C_nF_{2n}F$.

3. The process of claim 1 conducted in the presence of solvents or diluents that do not react with the reactants, catalyst or products.

4. The process of claim 3 wherein the solvent or diluent is selected from the group consisting of perfluoroalkanes, perfluoroethers and perfluoro tertiary amines.

5. The process of claim 1 wherein the solvent or diluent is the cyclic dimer of hexafluoropropene.

6. The process of claim 1 conducted at 20 degrees to about 200 degrees centigrade.

7. The process of claim 6 wherein the temperature range is about 50° C. to 150° C.

8. The process of claim 1 wherein the aluminum catalyst is a mixed halide containing F and at least one of Cl, Br or I.

9. The process of claim 8 wherein the catalyst is $AlF_nCl_{3-n}$, wherein n is from 0.05 to 2.95.

10. The process of claim 9 wherein n is from 2.5 to 2.95.

11. The process of claim 9 wherein the proportion of catalyst to $R_fCF_2I$ is 0.1 to 20 weight percent.

12. A process for the preparation of perfluorinated olefin of the structure

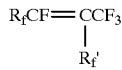
$$R_fCF = CCF_3$$
$$|$$
$$R_f'$$

wherein $R_f'$ is selected from the group consisting of F and $C_nF_{2n}F$ comprising:

(a) reacting perfluoroalkyliodide of the structure $R_fCF_2I$ with at least two moles tetrafluoroethylene in the presence of an aluminum chlorofluoride catalyst, where $R_f$ is $C_nF_{2n}F$, where n is 1–12 and $R_f'$ is selected from the group consisting of F and $C_nF_{2n}F$ where n is 1–12.

13. A process according to claim 12 wherein the product is perfluorobutene-2.

14. The process of claim 12 conducted in the presence of a solvent or diluent that is not reactive with reactants, catalyst or products.

15. The process of claim 12 wherein the solvent or diluent is selected from the group consisting of perfluoroalkanes, perfluoroethers and perfluoro tertiary amines.

16. The process of claim 12 wherein the solvent or diluent is the cyclic dimer of hexafluoropropene.

17. The process of claim 12 conducted at −10 degrees to about 200 degrees centigrade.

18. The process of claim 17 wherein the temperature range is about −10 to 100° C. wherein $R_f'$=F.

19. The process of claim 17 wherein the temperature range is about 50 to 150° C. wherein $R_f'$=$CF_3$.

20. The process of claim 12 wherein the aluminum catalyst is a mixed halide containing F and at least one of Cl, Br and I.

21. The process of claim 12 wherein the catalyst is $AlF_nCl_{3-n}$, wherein n is form 0.05 to 2.95.

22. The process of claim 21 wherein n is from 2.5 to 2.95.

23. The process of claim 12 wherein the proportion of $R_fCF_2I$ to $R_pCF=CF_2$ is between 1:1 and 1:100% on a molar basis and the amount of $AlF_nCl_{3-n}$ relative to $R_fCF_2I$ is between 0.1 and 20% on a weight basis.

* * * * *